US00PP24442P2

(12) United States Plant Patent
Warren

(10) Patent No.: US PP24,442 P2
(45) Date of Patent: May 13, 2014

(54) HYBRID OAK TREE NAMED 'JFS-KW2QX'

(50) Latin Name: *Quercus robur×alba*
Varietal Denomination: JFS-KW2QX

(75) Inventor: Keith S. Warren, Gresham, OR (US)
(73) Assignee: J. Frank Schmidt & Son Co., Boring, OR (US)

( * ) Notice: Subject to any disclaimer, the term of this patent is extended or adjusted under 35 U.S.C. 154(b) by 276 days.

(21) Appl. No.: 13/385,454

(22) Filed: Feb. 21, 2012

(51) Int. Cl.
*A01H 5/00* (2006.01)

(52) U.S. Cl.
USPC ..... Plt./225

(58) Field of Classification Search
USPC ..... Plt./225
See application file for complete search history.

*Primary Examiner* — Kent L Bell
(74) *Attorney, Agent, or Firm* — Klarquist Sparkman, LLP

(57) ABSTRACT

A variety of hybrid oak which combines fast first year growth, dense branching, a tightly fastigiate growth habit, and a narrowly columnar shape with deeply colored summer foliage and powdery mildew resistance.

10 Drawing Sheets

Latin name of the genus and species: *Quercus robur×alba*.
Variety denomination: 'JFS-KW2QX'.

ORIGIN OF THE NEW VARIETY

In 1991, I planted together in a row, seven upright and mostly narrow growing oaks of the of the species *Quercus robur* and hybrids of *Quercus robur* f. *fastigiata×alba*. Among these was an experimental selection that had been identified as *Quercus robur×alba* #7 (not patented). In the fall of 1996, I noticed that *Quercus robur×alba* #7 produced a crop of acorns. I collected these acorns and sowed them in a nursery seedbed in Boring, Oreg. They germinated in the spring of 1997. I grew these seedlings for two years in the seedbed and then planted a group of these seedlings in April, 1999, in a nursery row to grow for evaluation and possible selection. I subsequently selected a small group of 12 of these seedlings for further evaluation and transplanted them into a nursery row having wider spacing in February of 2002. The remaining seedlings not selected for the small group were destroyed. I evaluated these 12 selected trees during 2002 and 2003. In the fall of 2003, I selected 'JFS-KW2QX' as superior in appearance based on foliage qualities, narrow fastigiate form, and resistance to powdery mildew. In February 2004, I transplanted 'JFS-KW2QX' to a long term evaluation block. Of the other eleven trees, all were destroyed except one tree, named 'KW-7QRX' (not patented) that was kept for further evaluation. 'KW-7QRX' has a broadly oval form that is very different from 'JFS-KW2QX', and is believed to have a different pollen parent. The seed parent tree *Quercus robur×alba* #7 was destroyed in 2001 after determining that it was susceptible to powdery mildew and its form was broader, somewhat open, and not as desirable as 'JFS-KW2QX'.

I began trial asexual propagation of small plots of 'JFS-KW2QX' trees. I commenced this asexual propagation in August 2003 by successfully chip budding six trees onto *Quercus robur* rootstock. In 2004 I asexually propagated nine trees, in 2005 I asexually propagated seven trees, in 2006 I asexually propagated nine trees, in 2007 I asexually propagated 17 trees, and in 2008 I asexually propagated two trees. All propagation was done in nursery field rows in Canby, Oreg. by chip budding onto *Quercus robur* (not patented) rootstock. In each case, trees were grown for two or three years in nursery rows along side other oak varieties and observed and evaluated regularly. The trees that were asexually propagated in 2006 were transplanted in 2010 to another location in the Canby, Oreg. nursery. All of the other test trees were destroyed. From asexually propagated trees of my new variety, I established that my new variety possesses a unique combination of characteristics of fast first year growth, dense branching, a tightly fastigiate growth habit, and a narrowly columnar shape with deeply colored summer foliage and powdery mildew resistance and that these characteristics are firmly fixed in each successive generation.

SUMMARY

This new cultivar possesses a unique combination of characteristics in that it combines fast first year growth, dense branching, a tightly fastigiate growth habit, and a narrowly columnar shape with deeply colored summer foliage and powdery mildew resistance.

BRIEF DESCRIPTION OF THE DRAWINGS

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
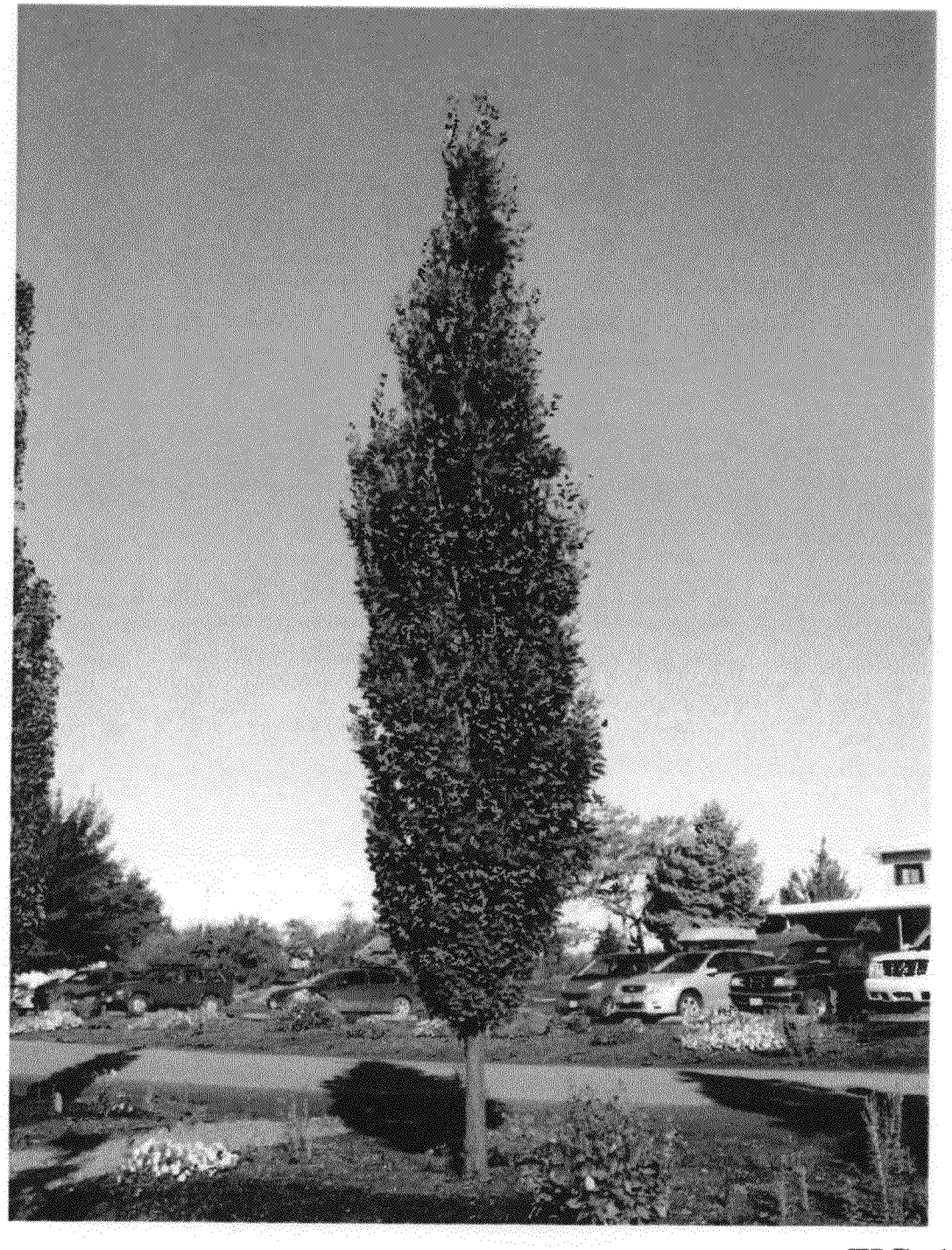
FIG. 1: Shows the original tree at 15 years of age in summer foliage. It shows the narrow columnar form, the density of branching, and the foliage color.
Figure 2:
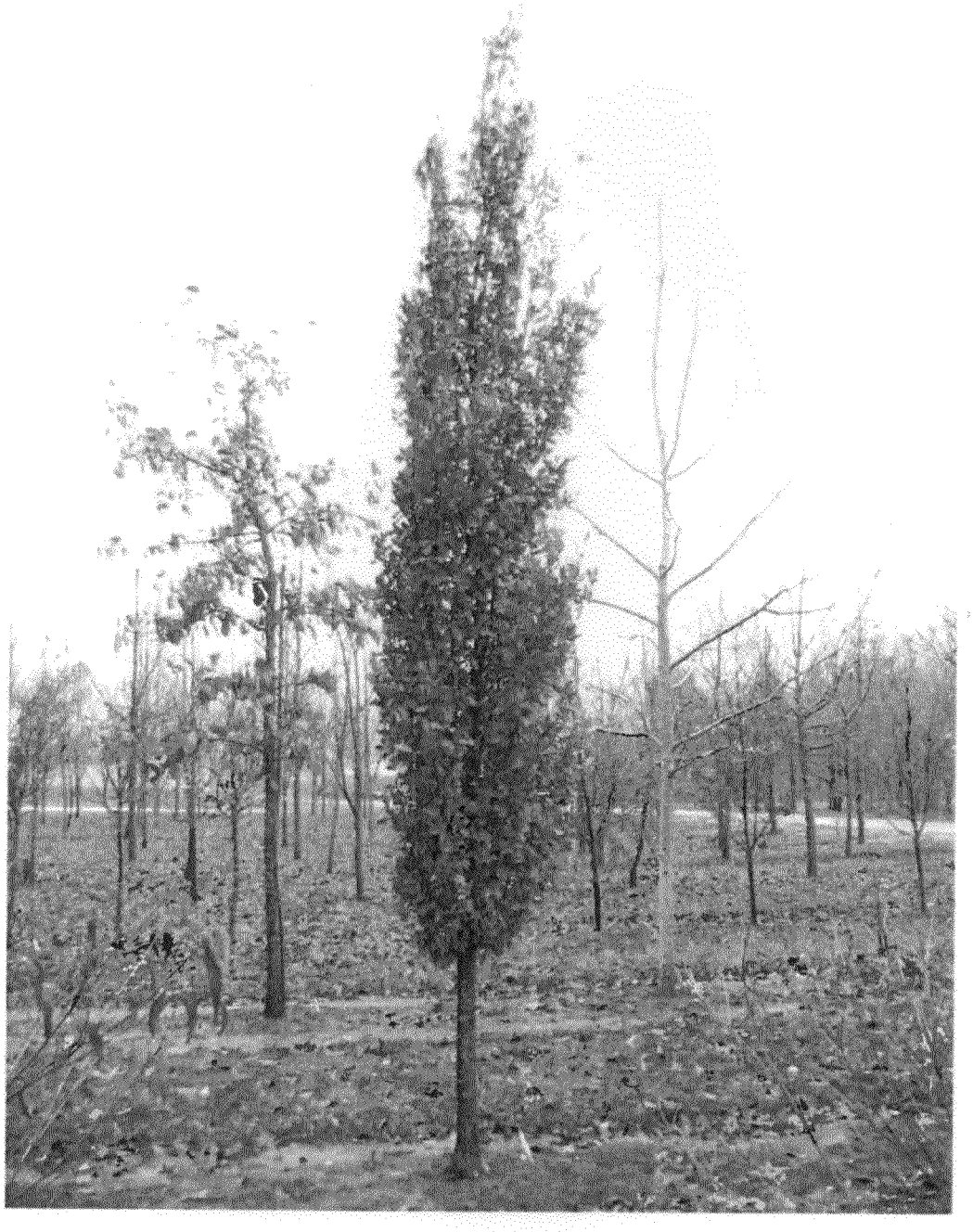
FIG. 2: Shows the original tree at 11 years of age illustrating the narrow columnar shape, the ascending branches, and amount of marcescent foliage held in early December.
Figure 3:
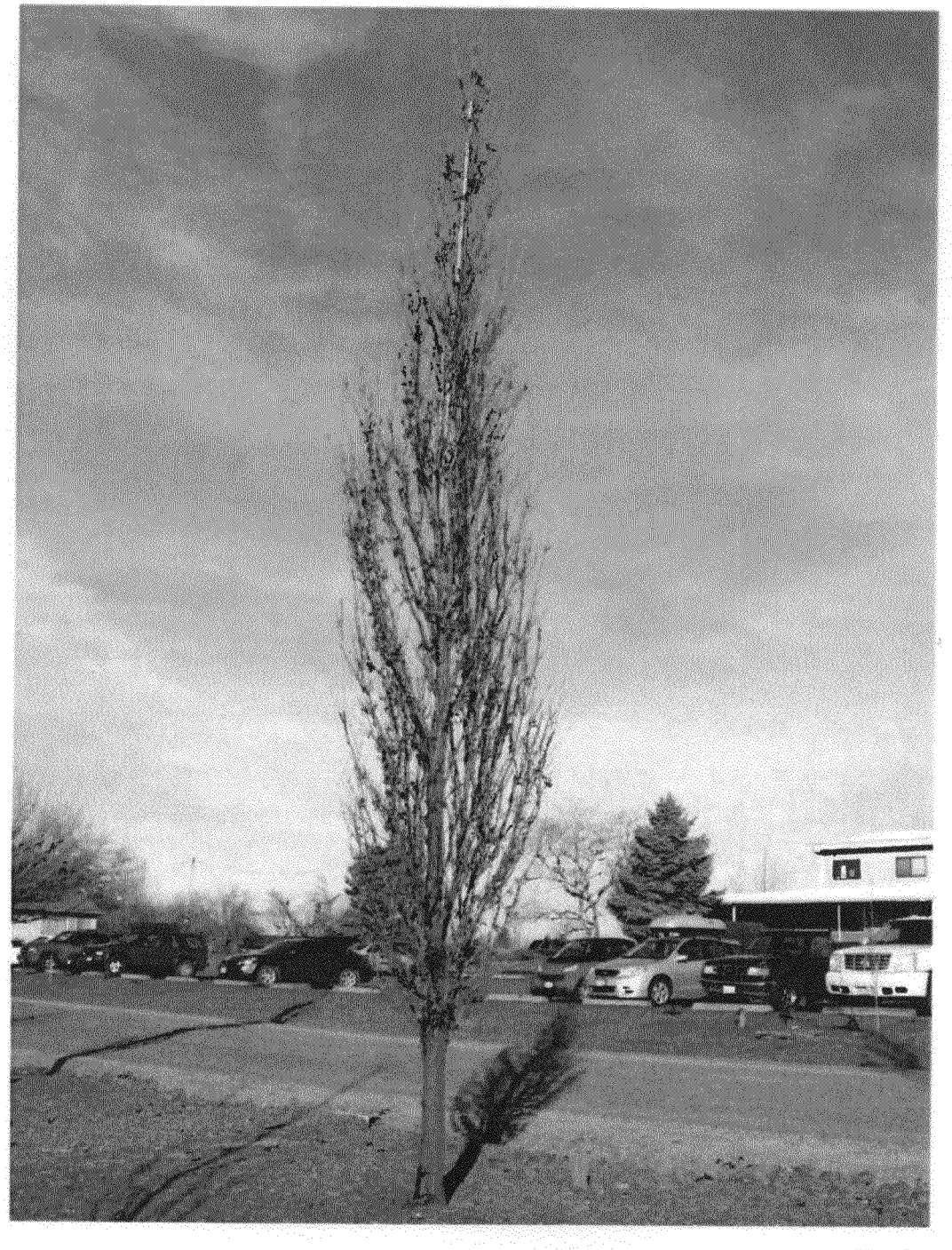
FIG. 3: Shows the original tree at 15 years of age in dormant condition in early February illustrating the fastigiate growth habit, the upward curving of branches, and the small amount of marcescent foliage still on the tree at this time of year.
Figure 4:
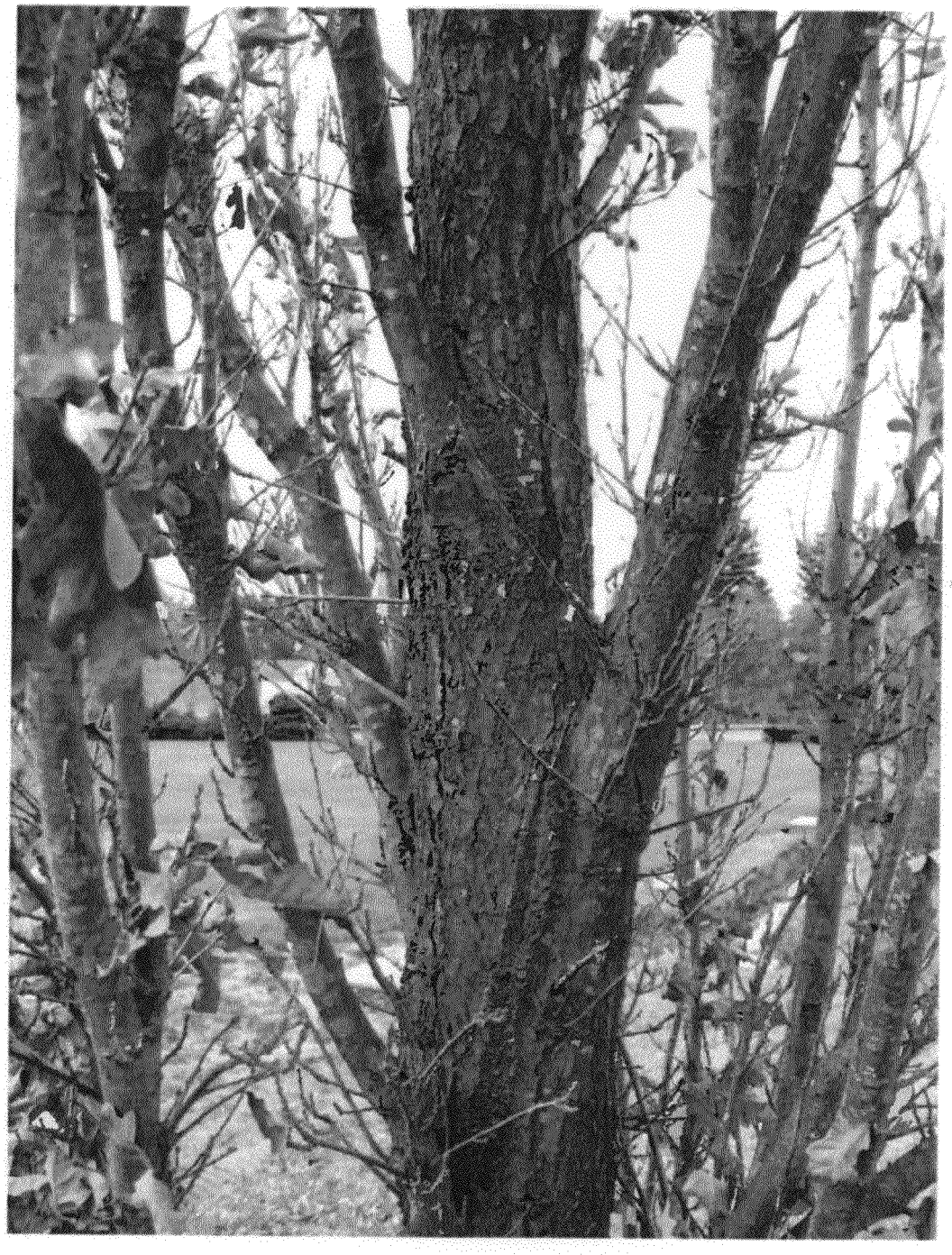
FIG. 4: Shows the branch angle of older branches on the original tree at 15 years of age.
Figure 5:
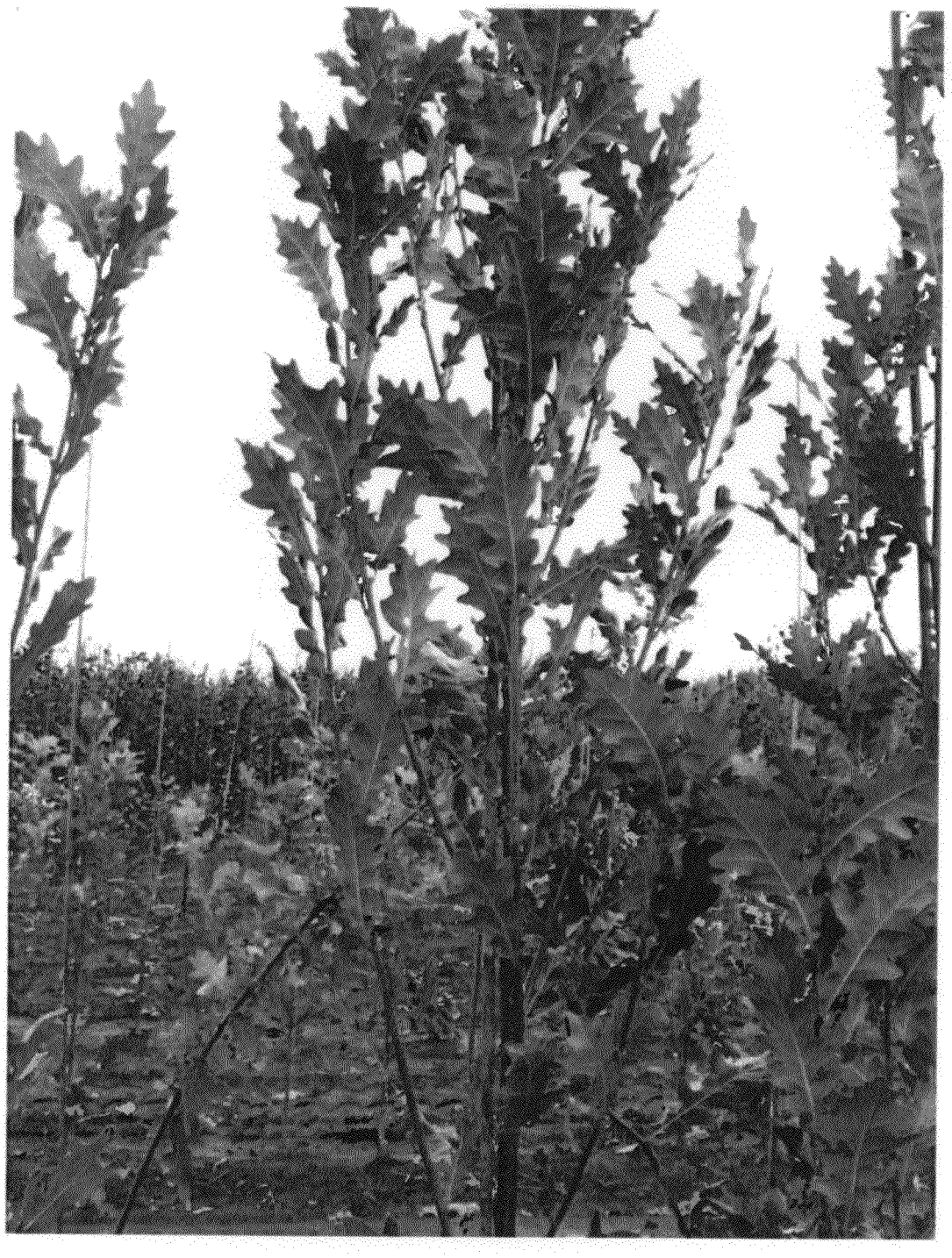
FIG. 5: Shows the branch angle and upsweeping and ascending nature of the new growth branches on a one year old propagated tree in a nursery row.
Figure 6:
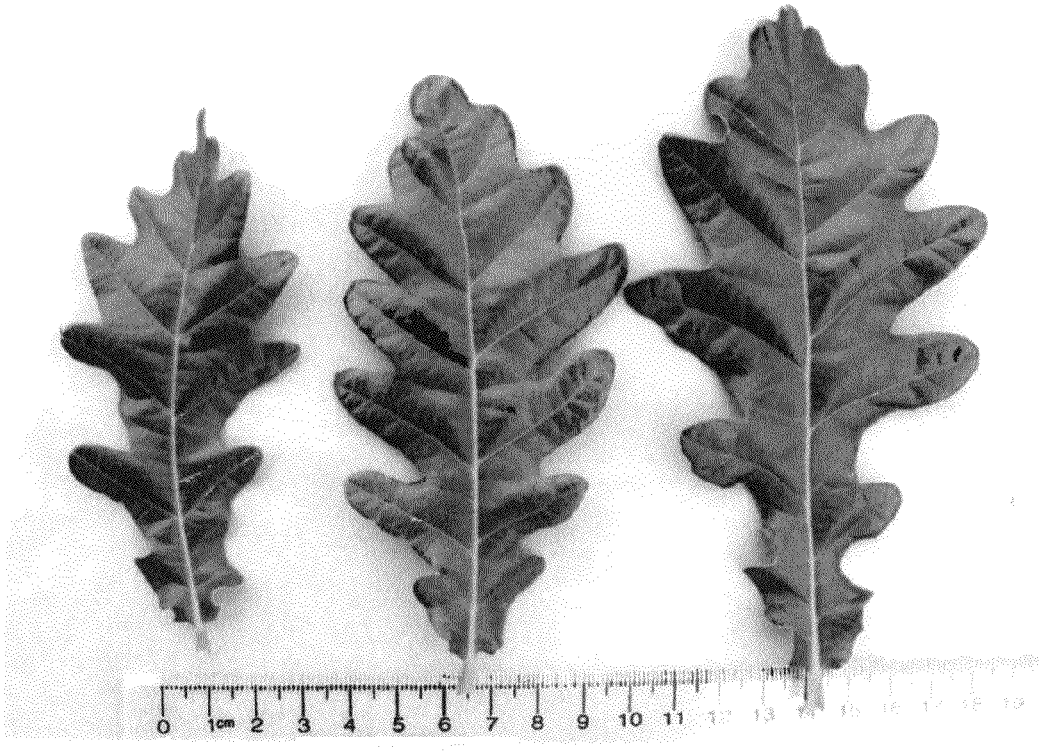
FIG. 6: Shows the upper surface of foliage in summer color.
Figure 7:
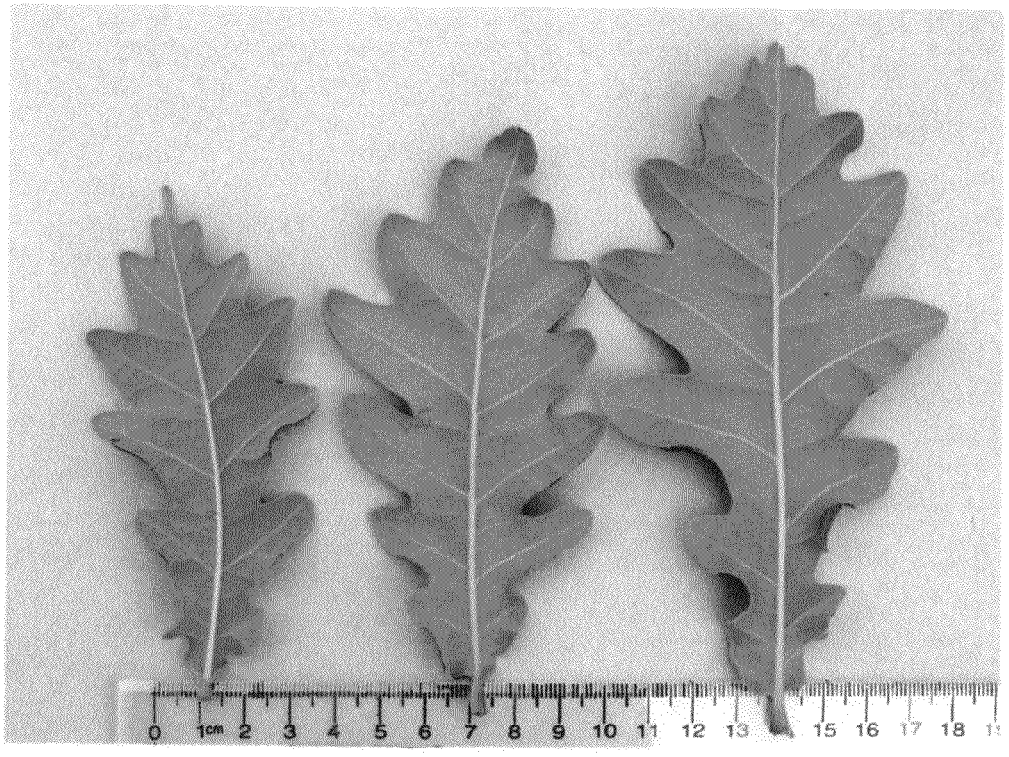
FIG. 7: Shows the lower surface of foliage in summer color.
Figure 8:
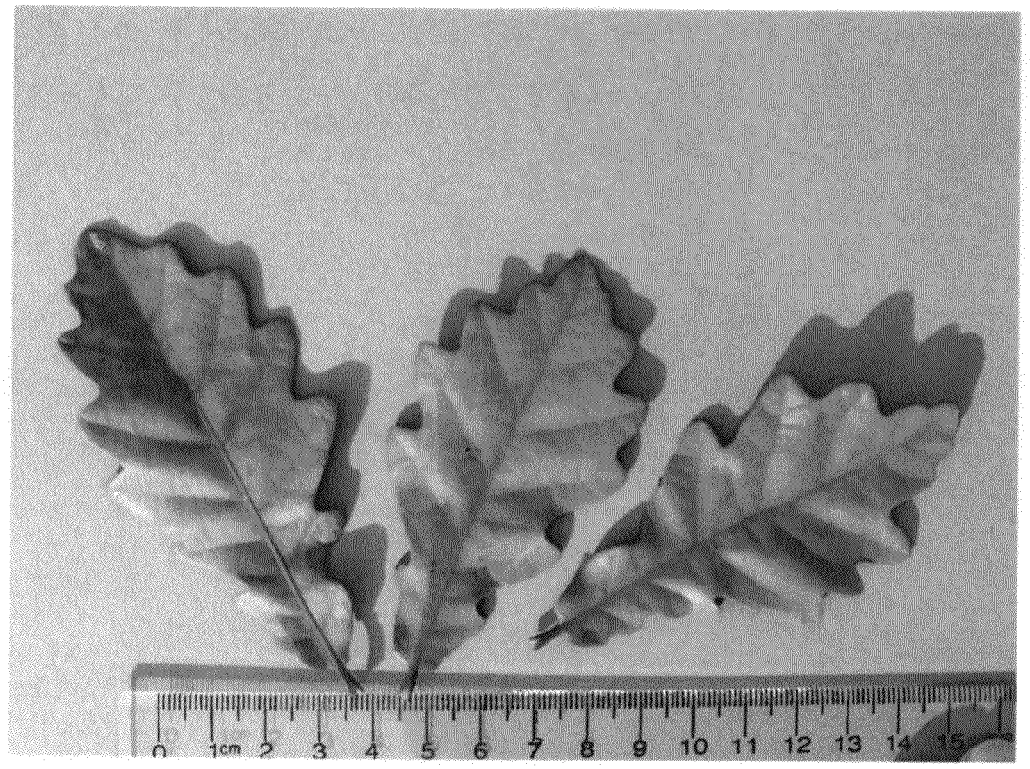
FIG. 8: Shows the upper surface of foliage in marcescent condition in early December.
Figure 9:
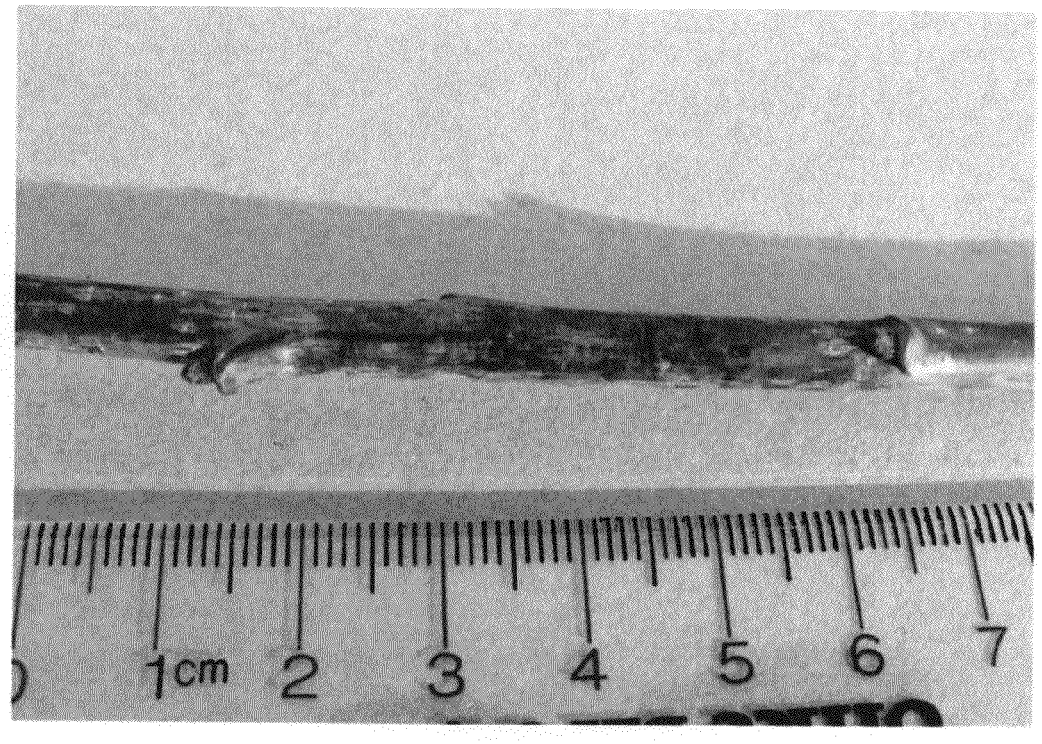
FIG. 9: Shows a dormant twig of a 2 year old propagated tree and winter buds.
Figure 10:
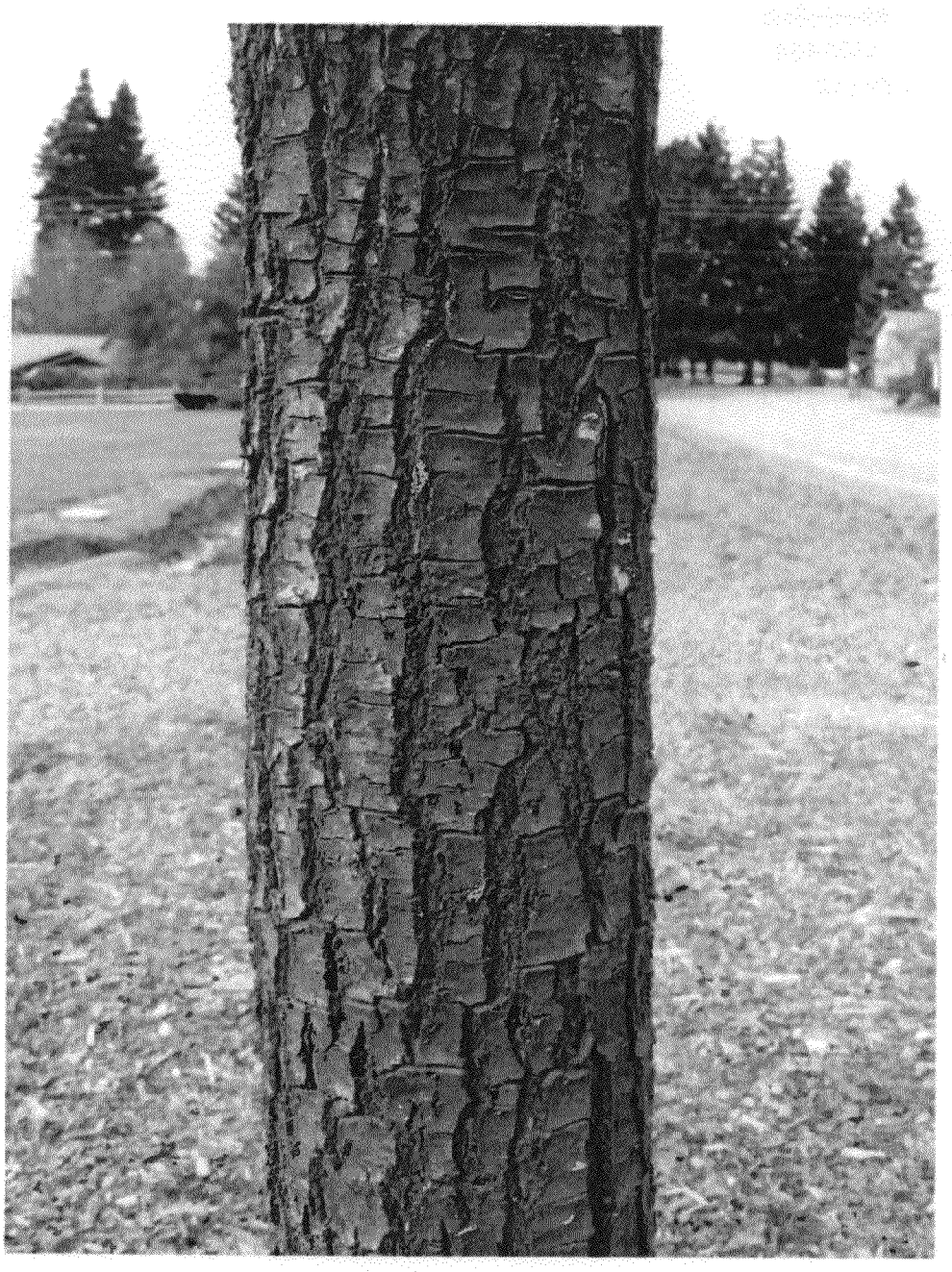
FIG. 10: Shows the bark of the original tree at 15 years of age illustrating the nature of the bark furrowing.

The following detailed description of the 'JFS-KW2QX' variety, with color terminology in accordance with The Royal Horticultural Society (R.H.S.), London, Colour Chart© 1986, and is based on observations of the original tree and of one and two year old progeny. The observed progeny were trees which were growing in Canby, Oreg.

Scientific name: *Quercus robur×alba* 'JFS-KW2QX'.

Parentage:

*Seed parent.*—*Quercus robur×alba* #7.

*Pollen parent.*—Unknown, but believed to be *Quercus robur* f. *fastigiata×alba* (not patented).

Tree:

*Overall shape.*—Tightly fastigiate growth habit with dense branching resulting in an extremely narrow, columnar shape.

*Height.*—Original tree: 7.3 meters at 15 years of age.

*Width.*—Original tree: 1.5 meters at 15 years of age.

*Trunk diameter.*—Original tree: 13.8 cm at 10 cm from ground; 11.9 cm at 1 meter, at 15 years of age.

*Trunk.*—Sturdy, very straight.

*Trunk bark texture.*—Mature tree: rough, strongly furrowed with numerous deep vertical furrows and a moderate number of horizontal furrows that create square plates of bark.

*Trunk bark color.*—Immature bark color: Grey-Brown 199B. Mature bark color: Greyed-Green 197A. Lenticels: None visible on trunk.

*Primary branches.*—Sturdy, long, strongly upright and ascending, curving gradually toward the vertical without a wavy growth pattern. Densely branching at a young age.

*Branch angle.*—Branch angle on a one year old tree is narrow, varying from 10 to 30 degrees, with branch tips oriented strongly upward at an angle of 10 to 20 degrees from the vertical. Branch angles on the original tree at 15 years of age begin at 25 to 40 degrees at the trunk junction and then branches gradually curve inward toward the trunk with branches angles becoming 0 degrees to 20 degrees off the vertical at the branch tips.

*Branch lenticels.*—Rounded to oval, 0.5 mm×0.5 mm to 1.0 mm×2.0 mm, White 155A as measured on one and two year old trees.

*Branch bark.*—The bark of young one year old branches varies with the growing season. In summer during active growth, one year old branches are Yellow-Green 144A with a tint of Greyed-Red 182B on the side most exposed to the sun. In autumn, branch bark turns Greyed-Green 195A to Greyed-Green 197B, and then matures to Brown 200A in the winter. Branch bark is smooth until the branch reaches about 3 cm diameter, at which time it starts to become furrowed.

*Dormant buds.*—Imbricate, rounded, 2.0 mm to 3.0 mm long by 2.0 mm in diameter. Greyed-Orange 166A to Brown 200C.

*Internodes.*—Internode length varies from 2.8 cm to 4.5 cm when measured on branches of one year old trees, average length 3.8 cm.

*Hardiness.*—Has tolerated temperatures to 10 degrees F. without damage in Boring, Oreg. and Canby, Oreg. It has not been tested at lower temperatures, but it is believed to have Zone 4 cold hardiness similar to other hybrids of the same species.

*Disease resistance.*—Resistant to powdery mildew (*Erysiphe alphitoides*). The original tree and asexually propagated trees have then been observed to be free of oak anthracnose (*Apiognomonia quercina*).

*Growth rate.*—Fast growing; more rapid growth as a 1 year tree in nursery rows than the growth of the most similar one-year old cultivars I have observed (see Table 1 below).

Leaves: Except as otherwise noted, observations are from twenty typical vigorous growth leaves.

*Arrangement.*—Alternate.

*Texture.*—Smooth on upper surface, mostly smooth below.

*Sheen.*—Moderately glossy.

*Length.*—11 cm to 16 cm when measured on two year old trees.

*Width.*—5 cm to 8 cm when measured on two year old trees.

*Petioles.*—5 mm to 9 mm long by 2 mm in diameter.

*Overall shape.*—Obovate with five to eight pairs of lobes. The sinuses between the lobes generally extend one-third to one-half of the distance to the mid-rib.

*Leaf orientation.*—Strongly upward.

*Margin.*—Lobed with acute to slightly rounded lobe tips.

*Tip.*—Acute.

*Base.*—Auriculate.

*Stipules.*—None.

*Veination.*—Pinnate.

*Spring leaf color.*—First emerging leaves are Yellow-Green 144A.

*Summer leaf color.*—Upper leaf surface: Green 131A to Green 139A. Lower leaf surface: Yellow-Green 146B to Yellow-Green 147B. Vein: Yellow-Green 146D.

*Fall leaf color.*—Fall color is Yellow-Orange 22A to Greyed-Orange 163B. In Boring, Oreg., the average dates of fall color are as follows. Color typically begins on October 30 and increases to peak on November 12, thereafter fading and ending in a marcescent condition on November 18. During the marcescent period, the foliage is Greyed-Orange 164B to Greyed-Orange 165B.

*Pubescence.*—None; the tree is glabrous.

*Persistence.*—The tree is deciduous, but marcescent in the late fall and early winter. During the marcescent period, foliage is gradually lost over the period from late November through March. Under Boring, Oreg. conditions, the tree typically reaches 50% defoliation by January 15 and completes defoliation by March 10, although these dates vary with winter weather conditions.

Flowers: The original tree and its progeny have not yet flowered.

Fruit: The original tree and its progeny have not yet set fruit.

Comparison to the species: 'JFS-KW2QX' is a hybrid cultivar. Although the pollen parent is unknown, it is believed that the cultivar is derived as a second generation seedling of trees originating from *Quercus alba* (not patented) and *Quercus robur* f. *fastigiata* (not patented) parentage. My cultivar differs from *Quercus alba* in that 'JFS-KW2QX' is fastigiate in growth habit and narrowly columnar in shape, whereas *Quercus alba* is broad spreading tree with wide branch angles, spreading branches, and a broadly oval to rounded shape. My cultivar differs from *Quercus robur* f. *fastigiata* in that f. *fastigiata* has a wavy growth pattern to its ascending branches whereas my cultivar's branches ascend smoothly with greater straightness and no wavy growth. Furthermore, my cultivar has a brighter and deeper looking summer leaf color, Green 131A to Green 139A on the upper leaf surface vs. Green 137C to Green 137A for f. *fastigiata*. In addition, my cultivar is resistant to powdery mildew while f. *fastigiata* is typically very susceptible.

Comparison to most similar cultivars: The most similar cultivars to 'JFS-KW2QX' are the hybrid cultivars 'JFS-KW1QX' and 'Crimschmidt' (U.S. Plant Pat. No. 9,103). 'JFS-KW1QX' (not patented) is a seedling from an acorn from a different tree than the seed parent for 'JFS-KW2QX', but has a similar hybrid species background. These most similar cultivars can be differentiated as shown in the table below, as determined by trees growing in adjacent rows in a Canby, Oreg. nursery.

TABLE 1

| 1 Year Tree Feature: | | | |
|---|---|---|---|
| | 'JFS-KW2QX' | 'JFS-KW1QX' | 'Crimschmidt' |
| Height, average | 177 cm | 152 cm | 128 cm |
| Average number of branches | 10 | 11 | 2 |
| Leaf color | Green 131A to Green 139A | Green 137A to Green 137B | Green 136A to Green 139A |
| Branch crotch angle | 10° to 30° | 40° to 60° | 20° to 40° |

I claim:

1. A new and distinct variety of hybrid oak tree, substantially as herein shown and described.

* * * * *